United States Patent [19]

Kaplan et al.

[11] Patent Number: 4,808,617

[45] Date of Patent: Feb. 28, 1989

[54] LYOPHILIZED OR PRECIPITATED CEPHALOSPORIN ZWITTERION AND SALT COMBINATION

[75] Inventors: Murray A. Kaplan, Syracuse, N.Y.; Nageswara R. Palepu, Dublin, Ohio; Joseph B. Bogardus, Manlius, N.Y.

[73] Assignee: Bristol-Myers Company, New York, N.Y.

[21] Appl. No.: 1,945

[22] Filed: Jan. 9, 1987

Related U.S. Application Data

[63] Continuation-in-part of Ser. No. 810,160, Dec. 18, 1985, abandoned.

[51] Int. Cl.$^4$ .................. A61K 31/545; C07D 501/46
[52] U.S. Cl. ...................... 514/202; 540/222
[58] Field of Search .................. 514/202; 540/222

[56] References Cited

U.S. PATENT DOCUMENTS

| | | | |
|---|---|---|---|
| 3,953,439 | 4/1976 | Gleason | 540/226 |
| 4,104,391 | 8/1978 | Cise | 540/227 |
| 4,406,899 | 9/1983 | Aburaki et al. | 540/222 |
| 4,604,386 | 8/1986 | Spry | 540/226 |

FOREIGN PATENT DOCUMENTS 2167302 11/1984 United Kingdom .

OTHER PUBLICATIONS

Kessler et al., "Comparison of a New Cephalosporin, BMY-28142, with Other Broad-Spectrum $\beta$-Lactam Antibiotics", *Antimicrobial Agents and Chemotherapy*, vol. 27, No. 2, pp. 207-216, Feb. 1985.

*Primary Examiner*—Robert Gerstl
*Assistant Examiner*—Mark W. Noel
*Attorney, Agent, or Firm*—David M. Morse

[57] ABSTRACT

Amorphous solid formed by lyophilization or cosolvent precipitation of an aqueous solution of 7-[$\alpha$-(2-aminothiazol-4-yl)-$\alpha$-(Z)-methoximinoacetamido]-3-[(1-methyl-1-pyrrolidinio)-methyl[-3-cephem-4-carboxylate zwitterion and a salt or mixture of salts from a selected particular group is a broad spectrum antibiotic composition and has better temperature stability at least up to 45° C. than the zwitterion. The salt is one wherein the cation is selected from the group consisting of sodium, lithium, calcium, and magnesium and the anion is selected from the group consisting of chloride, bromide, and iodide. The molar ratio of zwitterion to salt ranges from about 0.5:1 to about 2:1.

16 Claims, No Drawings

LYOPHILIZED OR PRECIPITATED CEPHALOSPORIN ZWITTERION AND SALT COMBINATION

CROSS-REFERENCE TO RELATED APPLICATION

This application is a continuation-in-part of our co-pending application Ser. No. 810,160 filed Dec. 18, 1985 now abandoned.

TECHNICAL FIELD

This invention is directed to elevated temperature stable semi-synthetic cephalosporin compositions.

BACKGROUND OF THE INVENTION

Aburaki et al. U.S. Pat. No. 4,406,899 discloses 7-[α-(2-aminothiazol-4-yl)-α-(Z)-methoxyiminoacetamido]-3-[(1methyl-1-pyrrolidinio)-methyl]-3-cephem-4-carboxylate in the zwitterion form and mentions corresponding acid addition salts and shows that the zwitterion form has broader spectrum activity than ceftazidime and cefotaxime. It refers to the zwitterion as 7-[(Z)-2-methoxyimino-2-(2-aminothiazol-4-yl)acetamido]-3-[(1-methyl-1-pyrrolidinium)methyl]-3-cephem-4-carboxylate.

Kessler et al., "Comparison of a New Cephalosporin, BMY-28142, with Other Broad-Spectrum β-Lactam Antibiotics", *Antimicrobial Agents and Chemotherapy*, Vol. 27, No. 2, pp. 207–216, February 1985 mentions the sulfate salt.

Kaplan et al. U.S. Ser. No. 762,235, filed August 5, 1985 discloses various acid addition salts.

The zwitterion and its acid addition salts are stable for approximately 8–16 hours as injectable compositions in aqueous solution at 24° C. The zwitterion even as a dry powder is unstable at room temperature and loses 30% or more of its activity on storage at elevated temperatures (e.g. 45° C. and above) for even one week and must be stored at −30° C. for adequate stability and therefore cannot be considered as appropriate for use under normal refrigeration conditions, i.e. those conditions available at pharmacies.

The aforementioned acid addition salts while possessing better temperature stability in the dry powder form than the zwitterion are too acidic for intramuscular and intravenous use and must be formulated with bases and/or buffering agents at pH 3.5–6.5 for such use.

SUMMARY OF THE INVENTION

It has been discovered herein that the amorphous solid formed by lyophilization or cosolvent precipitation of an aqueous solution of the zwitterion, i.e. 7-[α-(2-aminothiazol-4-yl)-α-(Z)-methoxyiminoacetamido]-3-[(1-methyl-1-pyrrolidinio)-methyl]-3-cephem-4-carboxylate zwitterion, and a salt or mixture of two or more salts selected from a particular group retains the broad spectrum antibiotic activity of the zwitterion but possesses improved temperature stability in dry powder form and when diluted to injectable concentration provides a pH of about 3.5 to about 7 and therefore is suitable for use for intramuscular and intravenous injection without the use of buffering agents or bases.

The salts for use herein are those wherein the cation is selected from the group consisting of sodium, lithium, calcium, and magnesium, and the anion is selected from the group consisting of chloride, bromide, and iodide. The salts are selected to provide an amorphous solid product with temperature stability such that it loses less than about 15–20% of its activity on storage in dry powder form at 45° C. for 2–4 weeks (1–2 weeks at 56° C.) as determined by HPLC assay.

The molar ratio of zwitterion to salt in the solution subjected to lyophilization or to cosolvent precipitation ranges from about 0.5:1 to about 2:1.

The compositions herein include the solvate-free form as well as the solvate form.

A preferred composition comprises an amorphous solid formed from zwitterion and sodium chloride. A more preferred composition comprises the above solid wherein the zwitterion and sodium chloride are in a 1:1 molar ratio. A still more preferred composition comprises the above-described 1:1 molar composition formed by lyophilization of an aqueous solution of the zwitterion and sodium chloride.

Another preferred composition comprises an amorphous solid formed from zwitterion and calcium chloride. More preferred compositions comprise the above solid wherein the zwitterion and calcium chloride are in a 1:0.5 or 1:1 molar ratio. Still more preferred compositions comprise the above-described 1:0.5 and 1:1 molar compositions formed by lyophilization of an aqueous solution of the zwitterion and calcium chloride.

Other preferred compositions comprise amorphous solids formed from zwitterion and a mixture of sodium chloride and calcium chloride.

A most preferred composition comprises an amorphous solid formed from zwitterion, calcium chloride and sodium chloride wherein the zwitterion, calcium chloride and sodium chloride are in a molar ratio of (a) 1:0.5:0.5 or (b) 1:0.1–0.2:0.8–1.0. Most preferably such a solid is formed by lyophilization of an aqueous solution of zwitterion, calcium chloride and sodium chloride.

A most preferred composition comprises an amorphous solid formed, preferably by lyophilization, from zwitterion, calcium chloride and sodium chloride wherein the zwitterion, calcium chloride and sodium chloride are in a molar ratio of 1:0.2:1. This solid appears to have the best combination of stability as a dry powder and in aqueous solution and pharmaceutical acceptability. In particular it possesses excellent dry powder stability at room temperature and at elevated temperatures and also has medically acceptable levels of calcium for human usage.

Another most preferred composition comprises an amorphous solid formed, preferably by lyophilization, from zwitterion, calcium chloride and sodium chloride wherein the zwitterion, calcium chloride and sodium chloride are in a molar ratio of 1:0.5:0.5. This solid appears to have excellent stability both in dry powder form and when reconstituted.

The term "cosolvent precipitation" is utilized herein to mean adding a non solvent to an aqueous solution of zwitterion and salt to coprecipitate these.

The term "dry powder" is used herein to mean a moisture content of less than 5% by weight.

The term "temperature stable" when used in describing compositions within the scope of the invention means a temperature stability such that less than about 15–20% activity is lost on storage in dry powder form at 45° C. for 2–4 weeks (1–2 weeks at 56° C.) as determined by HPLC assay.

The term "without the use of buffering agents or bases" means that the solid is reconstituted with sterile water and/or saline without further adjustment of the ambient pH with a pH adjusting substance.

DETAILED DESCRIPTION

The zwitterion used in forming the compositions herein has the following structural formula:

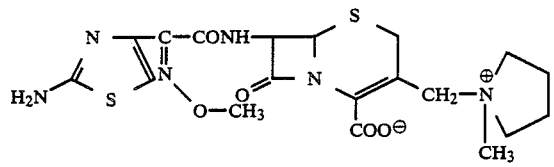

The zwitterion is readily prepared as described in Aburaki et al. U.S. Pat. No. 4,406,899.

Suitable salts for use in forming the compositions herein include, for example, sodium chloride, sodium bromide, sodium iodide, lithium chloride, lithium iodide, calcium chloride, calcium bromide, calcium iodide and magnesium chloride.

The molar ratio of zwitterion to salt preferably ranges from about 1:1 to about 2:1 and most preferably is about 1:1.

Subsequent to filing parent application Ser. No. 810,160 on Dec. 18, 1985, the present inventors found that suitable compositions could be formed from mixtures of the indicated salts as well as from the individual salts per se. The stability properties of such compositions will lie somewhere between the stabilities of the compositions formed from the individual salts used in the mixture. Thus, for example, one can prepare a solid from zwitterion, calcium chloride and sodium chloride and said solid will have stability properties intermediate between the zwitterion: NaCl and zwitterion:CaCl$_2$ compositions. Use of a mixture may be advantageous if one wishes to substantially obtain the favorable stability properties of a salt but, for physiological reasons, reduce the amount of that salt in the dosage form. In preparing compositions from two or more salts one simply employs the salts in amounts such that the total molar ratio is in the range indicated above, i.e. zwitterion:salt=0.5:1–2:1.

As previously indicated, one preferred composition herein is formed by lyophilization of an aqueous solution of said zwitterion and sodium chloride in a 1:1 molar ratio. This composition has an IR with no significant differences from the zwitterion. However, it has a differential scanning calorimetry decomposition point with an exotherm at about 197.4° C. compared with 173.84° C. for the zwitterion which indicates that it comprises a compound different from the zwitterion. While not being bound by theory for what is actually present, it is theorized that what is present is a complex with Na+ neutralizing the COO− of the zwitterion and Cl− neutralized by the N+ of the zwitterion, i.e. a compound with the following structure:

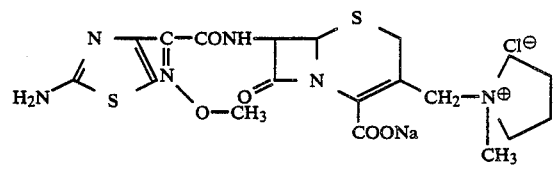

In view of this theoretical speculation, the composition herein formed from a solution of zwitterion and sodium chloride in 1:1 molar ratio will sometimes be referred to hereinafter as the Zwitterion:NaCl 1:1 Complex even though a complex has not been unequivocally proved.

The zwitterion:NaCl 1:1 Complex is very pharmaceutically acceptable. It has broad spectrum antibiotic activity substantially equal to that of the zwitterion. It has a satisfactory solution stability for a least 24 hours at 25° C. (at a concentration of 250 mg/ml of zwitterion in sterile water there is less than 10% loss in activity as determined by HPLC), and unlike the zwitterion, a satisfactory elevated temperature stability in dry powder form (about 10% loss upon storage at 45° C. for 4 weeks as determined by HPLC) and exceptional stability in dry powder form at normal refrigeration temperatures (no loss over 6 months at 4° C.). All during a 24 hour period after it is reconstituted to provide an injectable composition (i.e. after reconstitution to injectable concentration), the injectable composition maintains a satisfactory pH, i.e. ranging from about 4.2 to about 6.2 without the use of buffering agents or bases and is somewhat less toxic than the zwitterion.

We turn now to the preparation of the compositions herein.

As previously indicated one method of preparing the compositions herein is by lyophilizing under aseptic conditions an aqueous solution of zwitterion and salt. This is readily carried out, for example, by dissolving the zwitterion in sterile water to provide a concentration ranging from about 100 mg/ml to about 400 mg/ml, then introducing the aqueous zwitterion solution into a tank equipped with an agitator and agitating, then adding the salt or mixture of salts in the selected mole ratio amount and continuing agitation until dissolving is complete, e.g. for about 15 minutes to about 1 hour, then filtering, e.g. utilizing a sterilized filter assembly, then filling the filtered solution into vials and positioning these in lyophilization trays which are inserted into a lyophilizer, then freezing at −30° C. to −40° C. for a period ranging from about 4 hours to about 16 hours, then providing a vacuum ranging from 10 to 100 millitorrs and setting the temperature at −10° C. to −20° C. for 15 to 20 hours and then at 20° to 30° C. for 40 to 60 hours and condensing sublimate in a condenser at, e.g. −40° C. to −60° C.

As previously indicated, the other method for preparing the compositions herein is by cosolvent precipitation of an aqueous solution of zwitterion and salt. This is readily carried out under aseptic conditions, e.g. by forming an aqueous solution as set forth in respect to the lyophilization method but, instead of lyophilizing, admixing a non solvent to precipitate the zwitterion-salt complex, and separating the precipitate and drying. Normally it is optional whether to add the solution of zwitterion and salt to the non solvent or to add the non solvent to the solution of zwitterion and salt. The precipitate is readily separated, e.g. by filtering utilizing a sterilized vacuum filter assembly. Drying is readily carried out by high vacuum drying, e.g. at 40° to 60° C. The non solvent preferably is acetone or isopropanol but can be any pharmaceutically safe non solvent for zwitterion and salt which does not react with these.

The compositions herein are formed into injectable compositions by diluting with sterile water and/or saline to provide a composition with a zwitterion activity basis concentration ranging from about 1 mg/ml up to about 400 mg/ml as determined by HPLC assay, preferably from about 2.5 mg/ml up to about 250 mg/ml as determined by HPLC assay. Preferably dilution to 250 mg/ml is carried out utilizing sterile Water for Injection, U.S.P., and if further dilution is required by utilizing 0.9% Sodium Chloride Injection, U.S.P. For intramuscular or intravenous administration to an adult human, a total dosage of from about 750 to about 3000 mg per day in divided doses is normally sufficient.

The compositions herein are preferably shipped and stored in dry form under normal refrigeration conditions (e.g. at 4° C.) whereby they should remain more than 90% active for at least 1-2 years. They are readily converted to an injectable compositions by reconstitution, e.g. by a nurse or doctor, just prior to use.

The invention herein is illustrated in the following working examples.

EXAMPLE I

Synthesis and Testing of Zwitterion:NaCl 1:1 Complex

To a container equipped with an agitator was added 800 ml of aqueous solution containing 250 g of zwitterion. With the agitator running at medium speed, 30.41 g of NaCl was added to provide a 1:1 mole ratio of zwitterion:NaCl. Water for Injection U.S.P. was added qs to 1 L. Agitation of the solution as then continued for 15 minutes and for 5–10 minute intervals thereafter until sampling between agitating intervals showed no significant amount of undissolved particles. The resulting solution was transferred to a stainless steel pressure vessel and from there was passed, using nitrogen gas pressure, through a sterilizing filter assembly equipped with a prefilter and sterilizing filter into a clean sterilized container. Then 4 ml portions (1 g of zwitterion activity) was aseptically filled into 10 cc glass vials. After filling, the vials were loosely stoppered with lyophilization stoppers. The vials were then set into lyophilization trays which were inserted into a lyophilizer where the product was frozen for four hours at $-30°$ C. to $-40°$ C. The condenser on the lyophilizer was then set at $-60°$ C. $\pm 3°$ C. and the freezing unit was switched off. When the condenser temperature reached $-50°$ C., the vacuum pump was switched on. When the level of vacuum reached 200 microns, the shelf temperature was set at $-13°$ C. $\pm 3°$ C. which temperature was maintained for 16–18 hours. Then the shelf temperature was set at $\pm 25°$ C. and a temperature of 25° C. $\pm 2°$ C. was maintained for 48 hours. The lyophilizer was then inactivated and the vials were removed. The product was an amorphous solid which is characterized as zwitterion:NaCl 1:1 complex.

Analysis: Calculated for $C_{19}H_{24}N_6O_5S_2ClNa$: %C, 42.34; %H, 4.49; %N, 15.59; %S, 11.90, %H2O (KF), none; %Na (sulfated ash), 4.27; %Cl, 6.58. Found (corrected for H2O): %C, 41.96; %H, 4.57; %N, 14.73; %S, 12.28; %H2O (KF), 1.80; %Na (sulfated ash), 3.15; %Cl, 6.85.

No significant differences were noted by IR between the product herein and the zwitterion. However, the differential scanning calorimetry decomposition point was measured to exotherm at 197.4° C. which was noticeably different from that of the zwitterion (173.84° C.) indicating that the product herein is a different compound from the zwitterion.

Essentially the same product is obtained by adding 10–20 volumes of isopropanol to the clean sterilized container containing aqueous solution of zwitterion and sodium chloride to form a precipitate, separating the precipitate utilizing vacuum filtration, washing the precipitate with isopropanol and drying at high vacuum to obtain product in substantially dry form.

In evaluating the broad spectrum activity of the product herein, the Minimum Inhibitory Concentrations (MIC's) of the product herein and of the zwitterion were determined by the two-fold serial agar solution method in Mueller-Hinton agar and the data is presented in Table 1 below (wherein the Bristol A No. indicates a particular strain of microorganism):

TABLE 1

| | MIC Values (mg/ml) | | |
|---|---|---|---|
| | Bristol A No. | Zwitterion | Zwitterion:NaCl 1:1 Complex |
| 1. S. pneumoniae | A9585 | .016 | .016 |
| 2. S. pyogenes | A9604 | .008 | .008 |
| 3. S. faecalis | A20688 | 16 | 16 |
| 4. S. aureus | A9537 | .5 | .5 |
| 5. S. aureus/+50% serum | A9537s | 1 | 1 |
| 6. S. aureus/Pen. Res. | A9606 | 1 | 1 |
| 7. S. aureus/Meth. Res. 28° C. | A20699 | >125 | 125 |
| 8. E. coli | A15119 | .016 | .016 |
| 9. E. coli | A20341-1 | .016 | .03 |
| 10. K. pneumoniae | A9664 | .016 | .06 |
| 11. K. pneumoniae | A20468 | .5 | 1 |
| 12. E. cloacae | A9659 | .016 | .016 |
| 13. E. cloacae | A9656 | .03 | .06 |
| 14. P. mirabilis | A9900 | .008 | .016 |
| 15. P. vulgaris | A21559 | .03 | .03 |
| 16. M. morganii | A15153 | .008 | .016 |
| 17. P. rettgeri | A22424 | .13 | .25 |
| 18. S. marcescens | A20019 | .03 | .03 |
| 19. Ps. aeruginosa | A9843a | .5 | 1 |
| 20. Ps. aeruginosa/ Carb. Res. | A21628 | 2 | 2 |

The above data indicates the product formed herein, i.e. the Zwitterion:NaCl 1:1 Complex has substantially equivalent microbiological activity compared to the zwitterion. The zwitterion has been shown in Aburaki et al. U.S. Pat. No. 4,406,899 to have broad spectrum activity compared to ceftazidime and cefotaxime.

The toxicity of the Zwitterion:NaCl 1:1 Complex was tested by administration to Sprague-Dawley rats as a single intravenous bolus injection. The $LD_{50}$ for combined data from two studies was 796 mg/kg with 95% confidence limits between 759 and 832 mg/kg. This compares with an $LD_{50}$ of 669 mg/kg with 95% confidence limits of 618 and 732 mg/kg for the zwitterion. The response curves were parallel but the potency ratio indicated that the product herein was somewhat less toxic than the zwitterion.

Elevated temperature stabilities were determined by storing the Zwitterion:NaCl 1:1 Complex and the zwitterion in dry powder form and determining potency losses by HPLC. The potency losses are presented in Table 2 below. The specification of a range indicates the outside values in a plurality of runs.

TABLE 2

| | | Dry Stabilities | |
|---|---|---|---|
| | | | % Loss |
| Temperature | Time | Zwitterion | Zwitterion:NaCl 1:1 Complex |
| 4° C. | 1 month | | 0–1% |
| | 6 months | | None |
| 25° C. | 1 month | | 1–5% |
| | 5 weeks | | 3.0 |
| | 18 weeks | | 6–10% |
| 37° C. | 1 month | | 9–12.9 |

TABLE 2-continued

Dry Stabilities

| Temperature | Time | Zwitterion % Loss | Zwitterion:NaCl 1:1 Complex % Loss |
|---|---|---|---|
| | 5 weeks | | 6.0 |
| | 12 weeks | | 12.6 |
| | 4 months | | 9–18.0 |
| 45° C. | 1 week | 34.1 | 5.6 |
| | 2 weeks | | 8.3 |
| | 4 weeks | 71 | 10.7 |
| 56° C. | 1 week | 49.6 | 12 |
| | 2 weeks | | 16 |
| | 4 weeks | | 20 |
| 70° C. | 1 day | 34.4 | 12.7–23.0 |
| | 2 days | 46.2 | 21.7 |
| | 3 days | 55.2 | 34.0 |
| 100° C. | 1 day | 100 | 92 |

Aqueous solution stabilities for the Zwitterion:NaCl 1:1 Complex were determined by reconstituting to various concentrations and storing at 25° C. for time periods as stated. The reconstitution to 250 mg/ml (nominal) was with sterile Water for Injection, U.S.P. Further dilution was with 0.9% aqueous NaCl. Data is presented in Table 3 below wherein a range indicates the outside values in a plurality of runs.

TABLE 3

Stability In Aqueous Solution

| Concentration (mg/ml) | Time (hours) | % Remaining | pH |
|---|---|---|---|
| 250 | 0 | | 5.04–5.22 |
| | 3 | 100–102 | 5.03–5.24 |
| | 6 | 100–101 | 5.03–5.24 |
| | 24 | 92.7–96.0 | 5.14–5.39 |
| 50 | 0 | | 5.0–5.17 |
| | 3 | 99.4 | 5.07–5.31 |
| | 6 | 97–99.4 | 5.06–5.31 |
| | 24 | 93.2–94.7 | 5.30–5.60 |
| 10 | 0 | | 4.94–5.12 |
| | 3 | 99.5–100.1 | 5.05–5.34 |
| | 6 | 99.3–99.4 | 5.11–5.47 |
| | 24 | 95.2–97.0 | 5.44–5.78 |
| 2.5 | 0 | | 5.00–5.19 |
| | 3 | 100.0 | 5.28–5.66 |
| | 6 | 99.6–100.0 | 5.47–5.92 |
| | 24 | 96.2–96.8 | 5.87–6.18 |

The stability data indicate a satisfactory aqueous solution stability for at least 24 hours at 25° C. (room temperature).

EXAMPLE II

Synthesis and Testing of Composition From Zwitterion and Calcium Chloride 4.6 g of zwitterion was dissolved in 14 ml of water for injection containing 950 mg of $CaCl_2$ (1 molar equivalent).

The resulting solution was passed through a 0.22 micron sterile filter.

The filtrate was added under aseptic conditions with rapid stirring over a 5 minute interval to 400 ml of absolute ethanol. An amorphous precipitate formed. The mixture was slurried for 0.5 hours.

The solids were separated by vacuum filtration and washed with 40 ml of ethanol which was added to the filtrate (which is denoted herein filtrate A).

The ethanol-damp solids were slurried in 100 ml of absolute ethanol for 0.5 hours. The resulting amorphous solids were separated by vacuum filtration, washed with 20 ml of ethanol, 50 ml of ether and then high vacuum dried at 50° C. for four hours to provide 2.2 g of product containing zwitterion to $CaCl_2$ on an approximate 2:1 molar basis.

Analysis: Calculated for $C_{19}H_{24}N_6O_5S_2(Cl_2Ca)_{0.5}$: 42.56; %H, 4.51; %N, 15.68; %S, 11.96; %Cl, 6.6; %Ca as ash, 3.73. Found: %C, 38.4; %H, 4.85; %N, 13.76; %S, 8.82; %Cl, 5.44; %Ca as ash, 3.59; %H$_2$O (KF), 7.79. Found (dry basis): %C, 41.65; %N, 14.92; %S, 9.57; %Cl, 5.9; %Ca as ash, 3.89.

The filtrate A from above was concentrated under vacuum at 35° C. to 30 ml. A very dense cube-like microparticle showing no birefringence was obtained.

The dense solids were separated by vacuum filtration, washed with 15 ml of absolute ethanol and then with 20 ml of ether and dried as above to yield 2.0 grams of amorphous solid product approximating a zwitterion to $CaCl_2$ on a 1.5:1 molar basis (sesqui-zwitterion).

Analysis for $(C_{19}H_{24}N_6O_5S_2)_{1.5}$ $CaCl_2$: %C, 41.1; %H, 4.5; %N, 14.7; %S, 10.8; %Cl, 8.33; %Ca as ash, 4.8. Found: %C, 37.35; %H, 5.17; %N, 12.37; %S, 10.24; and %Cl, 7.84; %Ca as ash, 4.47; %H$_2$O (KF), 3.24; % ethanol, 0.5 mole. Found (H$_2$O and ethanol-free basis): %C, 40.01; %H, 4.88; %N, 13.3; %S, 10.57; and %Cl, 8.3; %Ca as ash, 4.7.

The ethanol soluble and insoluble complexes showed no significant differences in HPLC and UV spectra when compared to the zwitterion.

In evaluating the broad spectrum activity of the product herein, the Minimum Inhibitory Concentrations (MIC's) of the 1.5:1 molar ratio zwitterion:$CaCl_2$ product herein and of the zwitterion were determined by the two-fold serial agar dilution method in Mueller-Hinton agar and the data is presented in Table 4 below wherein the Bristol A No. indicates a particular strain of microorganism:

TABLE 4

MIC Values (mg/ml)

| | Bristol A No. | Zwitterion | Zwitterion:CaCl$_2$ 1.5:1 Molar Ratio Product |
|---|---|---|---|
| 1. S. pneumoniae | A9585 | .06 | .016 |
| 2. S. pyogenes | A9604 | .016 | .016 |
| 3. S. faecalis | A20688 | 16 | 16 |
| 4. S. aureus | A9537 | 1 | 1 |
| 5. S. aureus/+50% serum | A9537s | .5 | .5 |
| 6. S. aureus/Pen.-Res. | A9606 | 1 | 1 |
| 7. S. aureus/(METH.-RES.)28° C. | A20699 | 125 | 63 |
| 8. E. coli | A15119 | .016 | .016 |

TABLE 4-continued

| | MIC Values (mg/ml) | | |
|---|---|---|---|
| | Bristol A No. | Zwitterion | Zwitterion:$CaCl_2$ 1.5:1 Molar Ratio Product |
| 9. E. coli | A20341-1 | .03 | .016 |
| 10. K. pneumoniae | A9664 | .03 | .03 |
| 11. K. pneumoniae | A20468 | 1 | 1 |
| 12. E. cloacae | A9659 | .016 | .016 |
| 13. E. cloacae | A9656 | .13 | .25 |
| 14. P. mirabilis | A9900 | .008 | .008 |
| 15. P. vulgaris | A21559 | .03 | .03 |
| 16. M. morganii | A15153 | .008 | .008 |
| 17. P. rettgeri | A22424 | .03 | .03 |
| 18. S. marcescens | A20019 | .03 | .016 |
| 19. P. aeruginosa | A9843a | .5 | .5 |
| 20. P. aeruginosa/Carb. Res. | A21628 | 2 | 2 |

Elevated temperature stabilities were determined by storing the Zwitterion:$CaCl_2$ 1.5:1 molar ratio product and the zwitterion in dry powder form and determining potency losses by HPLC. The potency losses are presented in Table 5 below. In Table 5, the specification of a range indicates the outside values in a plurality of runs.

TABLE 5

| | | Dry Stabilities | |
|---|---|---|---|
| | | % Loss | |
| Temperature | Time | Zwitterion | Zwitterion:$CaCl_2$ 1.5:1 Molar Ratio Product |
| 37° C. | 2 months | | 3.5 |
| 45° C. | 1 week | 34.1 | 0.4–0 |
| | 2 weeks | | 3.2–5.7 |
| | 4 weeks | 71 | |
| 56° C. | 1 week | 49.6 | 0–5.3 |
| | 2 weeks | | 1.7–6.6 |
| | 4 weeks | | 13.7 |
| 70° C. | 1 day | 34.4 | |
| | 2 days | 46.2 | |
| | 3 days | 55.2 | 2.2–6.5 |
| 100° C. | 1 day | 100 | 20–30.0 |

EXAMPLE III

Testing of Other Compositions

Elevated temperature stabilities were determined by storing zwitterion:salt 1:1 molar ratio products and the zwitterion in dry powder form and determining potency losses by HPLC. The potency losses are presented in Tables 6 and 7 below. In Tables 6 and 7, the specification of a range indicates outside values in a plurality of runs.

TABLE 6

| | Dry Stabilities | | | | | |
|---|---|---|---|---|---|---|
| | % Loss | | | | | |
| | 100° C. | 70° C. | | | 56° C. | | |
| Salt added | 1 Day | 1 Day | 2 Days | 3 Days | 1 week | 2 weeks | 4 weeks |
| NONE (Zwitterion alone) | 100 | 34.4 | 46.2 | 55.2 | 49.6 | | |
| NaBr | | | | 17.1 | 20.0 | 20.2 | |
| NaI | | | | 14.5 | 14.0 | 17.1 | |
| $NaHSO_4$ | | | | 41.5 | | | |
| $CH_3SO_3Na$ | | | 15.5 | 22.3 | 30.8 | 46.6 | |
| $NH_2SO_3Na$ | | 18.6 | | | 41.1 | | |
| $NH_4Cl$ | | | | 63.0 | 43.4 | 50.3 | |
| LiCl | 3.2 | | | 8.6 | 0–9.0 | 2.5–10.0 | 17.0 |
| LiI | | | 3.1 | | | 3.1 | |
| $MgCl_2$ | 30–45.0 | | | 17–25.0 | 12.2 | | |
| $ZnCl_2$ | | 14.8 | | 18.8 | 20 | | |

TABLE 7

| | Dry Stabilities | | | | | | |
|---|---|---|---|---|---|---|---|
| | % Loss | | | | | | |
| | 45° C. | | | 37° C. | | | |
| Salt Added | 1 Week | 2 Weeks | 4 Weeks | 1 Month | 2 Months | 3 Months | 4 Months |
| NONE (Zwitterion alone) | 34.1 | | 71 | | | | |
| NaBr | 8.9 | 10.7 | | | | | |
| NaI | 7.9 | 8.4 | | | | | |
| $NaHSO_4$ | 19.9 | | | | | | |
| $CH_3SO_3Na$ | 12.6 | 21.6 | 28.9 | | | | |
| $NH_2SO_3Na$ | 18.1 | 25.5 | | | | | |
| $NH_4Cl$ | 9.0 | 196 | 33.5 | 19.6 | | | |
| LiCl | 0 | 0–4.5 | 6.4 | | 1.0 | 4.0 | 3.5 |
| LiI | | 0 | | | | | |
| $MgCl_2$ | 8.3 | | | | | | |
| $ZnCl_2$ | 10.3 | | | | | | |

Products containing the following salts on a 1:1 molar ratio basis provided percent losses of greater than 15–20% when stored at 45° C. for 2–4 weeks and 1–2 weeks at 56° C. and thus were not considered within the scope of the invention: NaF, $NaH_2PO_4$, $NaHCO_3$, $NaPO_2H_2$, $HOCH_2CH_2SO_3Na$, KCl, LiF and $FeCl_3$.

EXAMPLE IV

Compositions Using Salt Mixtures

Various lyophilized compositions formed from zwitterion and mixtures of NaCl and $CaCl_2$ were prepared and their temperature stabilities determined as in Examples 1-3. Table 8 below shows the potency remaining after HPLC assay of such compositions in comparison with compositions formed from single salts.

TABLE 8

Dry Stabilities
Formulations
% Potency Remaining

| Time Temperature | Zwitterion pH 5.1 | Zwitterion/NaCl 1:1 pH 4.9 |
|---|---|---|
| 1 d - 70° C. | 66 | 85.2 |
| 3 d - 70° C. | 54 | 76.6 |
| 1 w - 56° C. | 45-58 | 81.9 |
| 2 w - 56° C. | 39-43 | 73.9 |
| 4 w - 56° C. | — | 67.7 |
| 8 w - 56° C. | — | 55.9 |
| 1 w - 45° C. | 70 | 91.7 |
| 2 w - 45° C. | 49 | 87.5 |
| 4 w - 45° C. | 39 | 84.2 |
| 8 w - 45° C. | — | 76.2 |
| 13 w - 45° C. | — | 67.4 |
| 4 w - 37° C. | 69 | 90.4 |
| 8 w - 37° C. | — | 85.4 |
| 13 w - 37° C. | — | 80.9 |
| 13 w - 25° C. | — | 93.7 |

| Time/ Temperature | Zwitterion:CaCl$_2$ 1:1 pH 4.9 | Zwitterion:CaCl$_2$ 1:0.5 pH 4.6 |
|---|---|---|
| 1 d - 70° C. | 94.2 | 88.7 |
| 3 d - 70° C. | 88.8 | 80.8 |
| 1 w - 56° C. | 92.3 | 86.6 |
| 2 w - 56° C. | 86.9 | 78.4 |
| 4 w - 56° C. | 84.4 | 71.5 |
| 8 w - 56° C. | 79.0 | 62.5 |
| 1 w - 45° C. | 96.2 | 94.3 |
| 2 w - 45° C. | 93.0 | 89.2 |
| 4 w - 45° C. | 92.9 | 85.8 |
| 8 w - 45° C. | 88.9 | 80.4 |
| 13 w - 45° C. | 86.3 | 75.3 |
| 4 w - 37° C. | 95.2 | 92.0 |
| 8 w - 37° C. | 93.5 | 87.3 |
| 13 w - 37° C. | 91.1 | 85.8 |
| 13 w - 25° C. | 96.4 | 95.6 |

| Time/ Temperature | Zwitterion/CaCl$_2$/NaCl 1:0.5:0.5 pH 5.1 | Zwitterion:NaCl:CaCl$_2$ 1:0.8:0.2 pH 4.9 |
|---|---|---|
| 1 d - 70° C. | 94.7 | 91.4 |
| 3 d - 70° C. | 88.8 | 82.8 |
| 1 w - 56° C. | 93.3 | 89.0 |
| 2 w - 56° C. | 88.5 | 84.0 |
| 4 w - 56° C. | 82.6 | 76.3 |
| 8 w - 56° C. | 74.2 | 67.2 |
| 1 w - 45° C. | 98.1 | 95.8 |
| 2 w - 45° C. | 95.4 | 93.3 |
| 4 w - 45° C. | 91.3 | 88.9 |
| 8 w - 45° C. | 88.6 | 83.3 |
| 13 w - 45° C. | 85.3 | 79.3 |
| 4 w - 37° C. | 95.6 | 93.8 |
| 8 w - 37° C. | 92.6 | 90.6 |
| 13 w - 37° C. | 91.1 | 87.3 |
| 13 w - 25° C. | 97.4 | 96.7 |

| Time/ Temperature | Zwitterion:NaCl:CaCl$_2$ 1:0.8:0.2 pH 4.9 | Zwitterion:NaCl:CaCl$_2$ 1:1:0.2 pH 4.6 |
|---|---|---|
| 1 d - 70° C. | 91.0 | 91.6 |
| 3 d - 70° C. | 82.4 | 83.0 |
| 1 w - 56° C. | 88.7 | 89.8 |
| 2 w - 56° C. | 83.2 | 84.9 |
| 4 w - 56° C. | 77.4 | 78.4 |
| 8 w - 56° C. | 68.0 | 69.7 |
| 1 w - 45° C. | 95.4 | 93.7 |
| 2 w - 45° C. | 92.2 | 93.5 |
| 4 w - 45° C. | 88.9 | 89.8 |
| 8 w - 45° C. | 83.7 | 83.4 |
| 13 w - 45° C. | 81.2 | 80.3 |
| 4 w - 37° C. | 94.4 | 94.5 |
| 8 w - 37° C. | 90.9 | 90.6 |
| 13 w - 37° C. | 90.3 | 90.1 |

TABLE 8-continued

Dry Stabilities
Formulations
% Potency Remaining

| 13 w - 25° C. | 97.9 | 97.2 |
|---|---|---| d = days
w = weeks d=days w=weeks

Other variations will be evident to those skilled in the art. Therefore, the scope of the invention is intended to be defined by the claims.

We claim:

1. Temperature stable broad spectrum antibiotic composition which on dilution to injectable concentration provides a pH of about 3.5 to about 7 without the use of buffering agents or bases, said composition consisting essentially of (a) the amorphous solid formed by lyophilization or cosolvent precipitation of an aqueous solution of (i) 7-[-(2-aminothiazol-4-yl)-α-(Z)-methoximinoacetamido]-3-[(1-(methyl-1-pyrrolidinio)-methyl]-3-cephem-4-carboxylate zwitterion and (ii) a salt wherein the cation is selected from the group consisting of sodium, lithium, calcium, and magnesium and the anion is selected from the group consisting of chloride, bromide, and iodide, the molar ratio of zwitterion to salt in said solution ranging from about 0.5:1 to about 2:1, or (b) solvates thereof.

2. Antibiotic composition as recited in claim 1 wherein the cation is sodium.

3. Antibiotic composition as recited in claim 2 wherein the salt is sodium chloride.

4. Antibiotic composition as recited in claim 3 wherein the molar ratio of zwitterion to salt is about 1:1-2:1.

5. Antibiotic composition as recited in claim 4 wherein the amorphous solid is formed by lyophilization.

6. Antibiotic composition as recited in claim 5 having a differential scanning calorimetry decomposition point with an exotherm at about 197.4° C.

7. Antibiotic composition as recited in claim 1 wherein the anion is chloride.

8. Antibiotic composition as recited in claim 1 wherein the molar ratio of zwitterion to salt is about 1:1-2:1.

9. Antibiotic composition as recited in claim 1 wherein the amorphous solid is formed by lyophilization.

10. Antibiotic composition as recited in claim 8 wherein the salt is selected from the group consisting of sodium chloride, sodium bromide, sodium iodide, lithium chloride, lithium iodide, calcium chloride, calcium bromide, calcium iodide and magnesium chloride.

11. Temperature stable broad spectrum antibiotic composition which on dilution to injectable concentration provides a pH of about 3.5 to about 7 without the use of buffering agents or bases, said composition consisting essentially of (a) the amorphous solid formed by lyophilization or cosolvent precipitation of an aqueous solution of (i) 7-[α-(2-aminothiazol-4-yl)-α-(Z)-methoximinoacetamido]-3-[(1-methyl-1-pyrrolidinio)-methyl]-3zwitterion and (ii) a mixture of sodium chloride and calcium chloride salts, the molar ratio of zwitterion, calcium chloride and sodium chloride in said solution being (a) about 1:0.5:0.5 or (b) about 1:0.1-0.2:0.8-1.0.

12. Antibiotic composition of claim 11 wherein the molar ratio of zwitterion, calcium chloride and sodium chloride is 1:0.5:0.5

13. Antibiotic composition of claim 11 wherein the molar ratio of zwitterion, calcium chloride and sodium chloride is 1:0.1–0.2:1.0.

14. Antibiotic composition of claim 11 wherein the molar ratio of zwitterion, calcium chloride and sodium chloride is 1:0.1–0.2:0.8–0.9.

15. Antibiotic composition of claim 11 wherein the molar ratio of zwitterion, calcium chloride and sodium chloride is 1:0.2:1.

16. Antibiotic composition of claim 11, 12, 13, 14 or 15 wherein the amorphous solid is formed by lyophilization.

* * * * *